United States Patent [19]

Barton

[11] Patent Number: 4,869,339

[45] Date of Patent: Sep. 26, 1989

[54] HARNESS FOR SUPPRESSION OF HEARING AID FEEDBACK

[76] Inventor: James I. Barton, 23915 Danzig Bay, Laguna Niguel, Calif. 92677

[21] Appl. No.: 255,313

[22] Filed: Oct. 11, 1988

Related U.S. Application Data

[63] Continuation-in-part of Ser. No. 191,078, May 6, 1988, abandoned.

[51] Int. Cl.[4] .......................... A61B 7/02; H04R 25/02

[52] U.S. Cl. .................................... 181/130; 181/135; 381/68.6; 381/69; 381/188; 381/189; 381/205

[58] Field of Search ........................ 181/130, 132, 135; 381/68.6, 69, 69.1, 69.2, 188, 189, 205

[56] References Cited

U.S. PATENT DOCUMENTS

| | | | |
|---|---|---|---|
| 2,513,985 | 7/1950 | Woodruff et al. | 381/187 |
| 2,908,343 | 10/1959 | Hummert | 181/130 |
| 3,130,810 | 4/1964 | Werner | 181/135 |
| 3,448,224 | 6/1969 | Giller | 381/68.6 |
| 3,539,032 | 11/1970 | Scanlon | 181/135 |
| 4,539,440 | 9/1985 | Sciarra | 381/68.6 |
| 4,540,063 | 9/1985 | Ochi et al. | 181/135 |
| 4,696,045 | 9/1987 | Rosenthal | 381/189 X |

*Primary Examiner*—B. R. Fuller
*Attorney, Agent, or Firm*—Charles D. Brown

[57] ABSTRACT

A generally tubular cylinder of resilient material such as a silicon rubber, for mounting over a hearing aid, or ear plug, so as to provide two gaskets which seal the hearing aid, or ear plug, against the skin of the ear canal and stabilize it against movement in the ear canal thereby suppressing acoustical feedback. The cylinder is further shaped to provide a tab which extends to the exterior of the ear canal so that it can be easily grasped by the user to remove the hearing aid.

One of the ends (or gaskets) of the hearing aid harness may be lengthened to extend beyond and away from that end of the hearing aid which houses the speaker.

22 Claims, 4 Drawing Sheets

HARNESS FOR SUPPRESSION OF HEARING AID FEEDBACK

This is a continuation-in part of application Ser. No. 07/191,078, filed May 6, 1988, now abandoned.

FIELD OF THE INVENTION

This invention relates to hearing aids and in particular to a harness-like device which is mounted upon a hearing aid (or an earplug) in a manner to stabilize its position within the ear and thereby permit use of higher gain without producing acoustic feedback.

BACKGROUND

One of the most persistent and annoying problems facing users of hearing aids is feedback, which is perceived by the user as a high pitched high volume whistling in the ear. Feedback can be a problem with behind-the-ear hearing aids but is particularly prevelant with in-the-ear hearing aids where the microphone and the speaker are in relatively close proximity. Various approaches to solving the feedback problem have been taken, including electronic filter circuits, peak control circuits (U.S. Pat. No. 4,689,818), adaptive noise suppressors (U. S. Pat. No. 4,658,426), microprocessor controlled hearing aids (U.S. Pat. No. 4,596,902), clipping circuits (U.S. Pat. No. 4,506,113), notch filters (U.S. Pat. No. 4,232,192) and other amplifier related circuits. Each of these electronic approaches results in a more complicated hearing aid design and increased cost. Various mechanical approaches have also been taken such as earmolds and hollow cylinder gaskets. Earmolds must be custom fitted to each user's uniquely shaped ears, are quite expensive and can require multiple visits to a doctor's office before a satisfactory fit is achieved. Gaskets and O-rings tend to slide off the narrow end of the hearing aid when the hearing aid is removed from the ear. This tendency is exacerbated by perspiration, ear wax or other lubricants that find their way between the hearing aid and the gasket or O-ring. An O-ring or gasket that slips off can easily get lost or even worse can pose a serious medical problem if it gets trapped or lost inside the ear canal. U.S. Pat. No. 2,521,414 to Schier shows an insert intended to be placed over the tip of a hearing aid for placement within the ear canal, and U. S. Pat. No. 3,080,011 shows an insert to be placed over the tip of the tube of a behind the ear hearing aid.

SUMMARY OF THE INVENTION

A generally tubular cylinder of resilient material, such as a silicon rubber, is formed for slipping over a hearing aid, or ear plug, so as to provide two gaskets which seal the hearing aid, or ear plug, against the skin of the ear canal thereby blocking and suppressing acoustic feedback. The cylinder is further shaped to provide a tab which extends to the exterior of the ear canal so that it can be easily grasped by the user's fingers to facilitate removal of the hearing aid. These and other advantages of the invention will become apparent upon reading the detailed description below and consideration of the drawings.

DETAILED DESCRIPTION OF THE INVENTION

Figure 1:
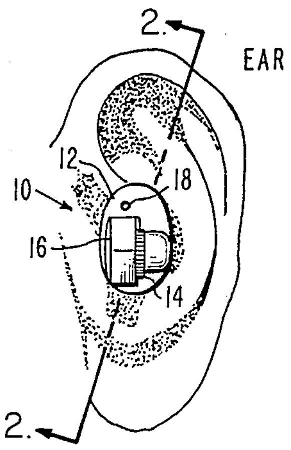
FIG. 1 shows an in-the-ear hearing aid in the ear of a wearer.
Figure 2:
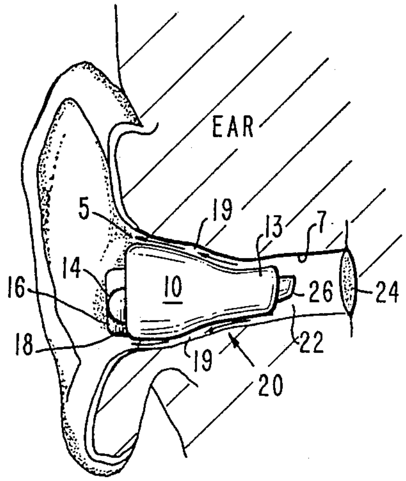
FIG. 2 is a cross section taken along the line 2—2 of FIG. 1.

Today's in-the-ear hearing aid is used by inserting the hearing aid into the entrance 5 of the ear canal 7 as shown in FIGS. 1 and 2. The hearing aid 10 generally has an oval outer end 12 on which are located the various devices necessary to control and maintain the hearing aid. These include the volume adjust mechanism which may take the form of a knurled wheel 14 which is internally connected to circuitry to raise and lower the gain of the hearing aid. A door 16 opens to permit access to the battery for replacement purposes. The microphone 18 collects sound waves and converts them into electrical signals for amplification on the interior of the hearing aid.

As best shown in FIG. 2, the hearing aid 10 is shaped to generally conform to the shape of the chamber 20 located at the entrance 5 of the ear canal 7. Persons with larger chambers 20 are fitted with larger hearing aids. Some hearing aids are available in only a limited nember of "standard" sizes. This, together with the fact that no two chambers are shaped exactly alike, means that there can never be a "perfect match" between the shape of the standard hearing aid and the shape of a given person's chamber 20. Thus, in the absence of custom molding and shaping which is very time consuming and expensive, there will usually be one or more open passageways 19 from the inner portion of the ear canal (such as at 22) to the exterior of the ear in the vicinity of the microphone 18.

Acoustic energy from a source not shown impinges on microphone 18. The acoustic energy is converted to electrical energy, provided to an amplifier within the hearing aid where it may be greatly amplified and provided to a speaker located inside the small end 13 of the hearing aid. A tubular appendage 26 may be provided as shown to keep the passageway clear. The amplified sound waves enter the ear canal 7 and travel to the eardrum, but they also travel back through passageway 19 between the walls of chamber 20 and the outside walls of hearing aid 10 as indicated by the arrows and exit the ear at 26. Some of the acoustic energy exiting as at 26 may then re-enter microphone 18. If the amplitude of the acoustic energy re-entering microphone 18 is sufficiently high the classic self sustaining feedback situation will result. The input to the microphone is increased (by the re-entering sound) resulting in increased output volume. The output volume thus quickly increases to the point where a screeching high volume, painful signal is broadcast to the wearer's eardrum and interferes with speech discrimination Feedback is only one of a number of problems that affect users of hearing aids. Because the hearing aid conforms to the shape of the chamber 20 which has an entrance larger than its inner/bottom end, the hearing aid can easily work its way out of the chamber. Perspiration and ear wax serve to lubricate the surfaces. Any slight muscle movement around the ear canal, such as caused by prolonged talking, yawning, grinding teeth or eating, may easily dislodge the hearing aid and move it outward from its proper position for most effective operation. As the hearing aid moves outward, small clear passageways 19 are produced and feedback occurs. This results in the user having to repeatedly reseat the hearing aid in the ear or decrease the gain of the hearing aid in order to avoid feedback. But by decreasing the gain, the user's hearing ability is decreased. Also if the hearing aid becomes sufficiently loose, it may fall out and be damaged or lost.

Figure 3:
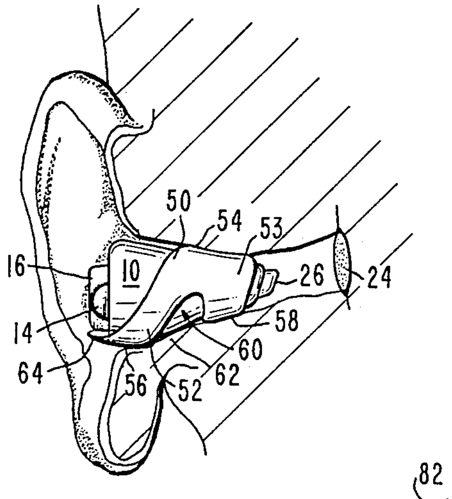
FIG. 3 shows a harness of the present invention in place upon the hearing aid as worn in the user's ear.

Each of the above problems is solved by a feature or combination of features of the present invention. FIG. 3 shows the invention in place on a hearing aid and seated in the chamber 20 of a user's ear. Feedback is prevented by the dual gasket effect of the harness 50. A first gasket 52 is formed by that portion of harness 50 connecting gasket wall 54 and gasket wall 56. A second gasket 53 is formed by that portion of harness 40 connecting gasket wall 54 and gasket wall 58. Since the gaskets are resilient and snug fitting, they effectively block any formation of a clear passageway 19 for acoustic energy to leave the speaker and re-enter the microphone 18.

The shape of the harness 50 also prevents the hearing aid from working loose in the ear canal as a result of talking, yawning and eating. Between the two gasket walls 56 and 58 is a notch 60. The presence of the notch 60 allows the skin of the ear canal to form a slight bulge or ridge 62 in the notch. The ridge 62 assumes a locking relationship with the second gasket 53 which is sufficient to keep the hearing aid from working loose even during prolonged conversations and chewing. An additional benefit of the particular shape of the harness 50 is the presence of tab 64 which provides a user with a convenient "handle" with which to pull the hearing aid 10 out of the ear. Because each gasket is securly connected to the tab 64, there is no danger of a gasket falling off the small end 13 of the hearing aid and becoming trapped or lost in the ear canal.

Figure 4:
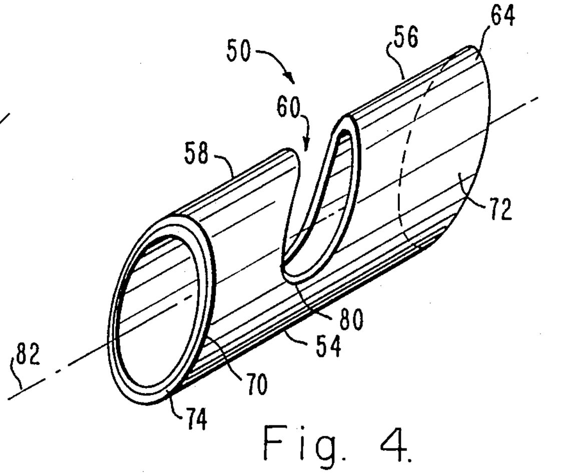
FIG. 4 is a perspective view of the invention.

The harness 50 is shown in its free state, i.e. not stretched and not mounted in place on a hearing aid, in FIG. 4. The harness is generally tubular in shape. For proper fitting and comfort, the beveled end 70 has a smaller outside diameter than does the opposite end 72. Hence, the shape of harness 50 can be loosely described as slightly conical. Also for comfort reasons, a beveled edge 74 is provided on end 70 so that when placed and seated in the ear a sharp right angle edge is avoided. The opening of end 70 is formed to be approximately perpendicular to the longitudinal centerline 82 and hence is circular. Intermediate the ends of harness 50 is a notch 60. The depth of the notch is not critical. However, it must be deep enough to provide sufficient flexibility to the harness to permit stretching and fitting over the hearing aid. Also the notch should not be so deep as to produce a wall 54 so thin that it will tear during fitting and stretching. A notch depth of between thirty and sixty percent of the diameter of the tubular member is preferred. In order to resist tearing during the stretching of the harness to fit it over the hearing aid, the bottom of the notch is provided with a smooth radius curve 80.

The opening in the opposite end 72 is formed to be at an angle of approximately 30 to 60 degrees with respect to the longitudinal centerline 82 of the harness. This produces a small inconspicuous tab 64 which can easily be grasped by the wearer to facilitate removal of the hearing aid from the ear.

To demonstrate the effectiveness of the harness to reduce the tendency of the hearing aid to work loose during chewing, talking and other similar muscle movement, hearing tests were conducted on a patient. Each of FIGS. 5 through 8 shows the results of those tests for both the right ear (X's) and the left ear (dots).

First, a patient was fitted with a properly inserted and seated hearing aid but without a harness. A hearing test was conducted just prior to dinner. The results of the test are shown in FIG. 5 and will serve as a baseline reference for the data presented in FIG. 6.

Figure 6:
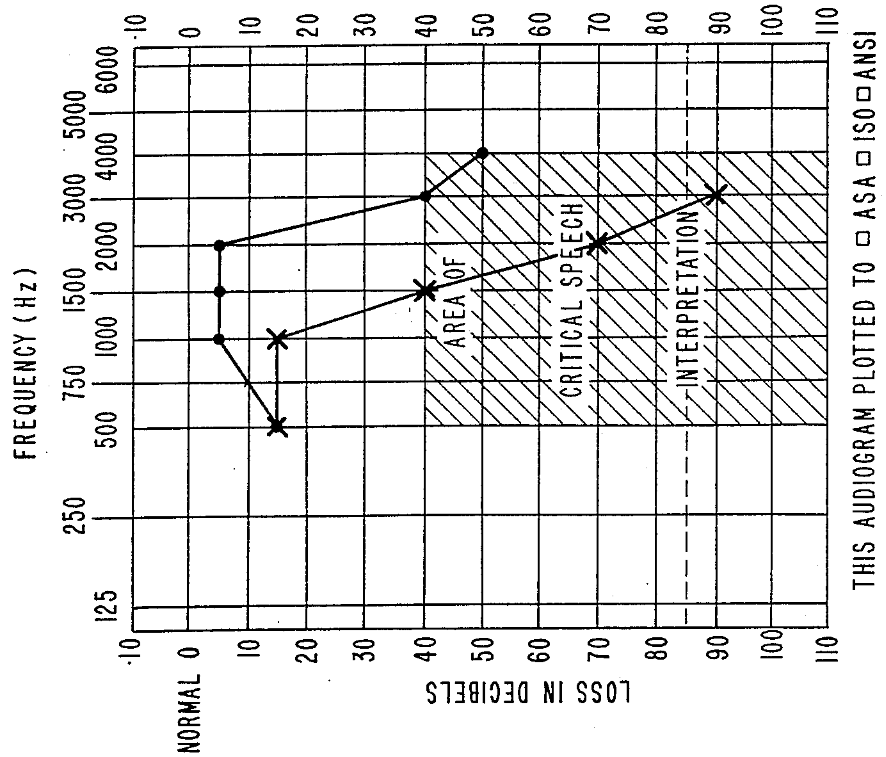
FIG. 6 is a graph of the hearing ability of the same patient, measured with a hearing aid, after dinner, and with no harness used.

Next, the same patient ate a full meal and engaged in some conversation for a total time of approximately sixty minutes. During the course of the meal the hearing aid worked loose and created clear feedback passageways. The gain of the hearing aid therefore had to be reduced, as compared to its setting just prior to the meal, in order to prevent feedback. After the meal another hearing test was conducted with the gain set at the required reduced level to avoid feedback. Those results are shown in FIG. 6. A casual comparison of FIG. 5 with FIG. 6 is sufficient to appreciate the degree to which hearing was impaired as a result of the movement of the hearing aid and the consequent reduction in gain required to avoid feedback. It is worth noting that the hearing in the left ear has not sufficiently changed from that shown in FIG. 5. However, the hearing has been significantly reduced in the right ear. It was only after the test results were reviewed that the patient pointed out that he chews almost exclusively on the right side of his mouth. This results in far more muscle movement near the right ear and hence more movement of the hearing aid and a greater tendency for feedback in the right ear. Thus the gain had to be reduced much more for the hearing aid in the right ear.

Figure 5:
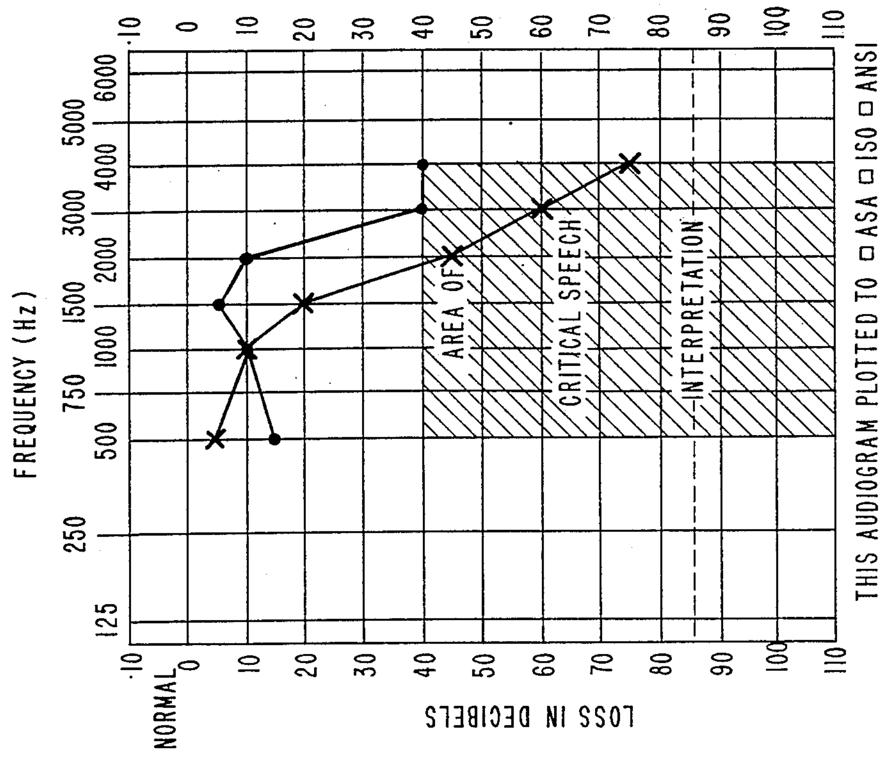
FIG. 5 is a graph of the hearing ability of one patient, measured with a hearing aid, before dinner, and with no harness used.
Figure 8:
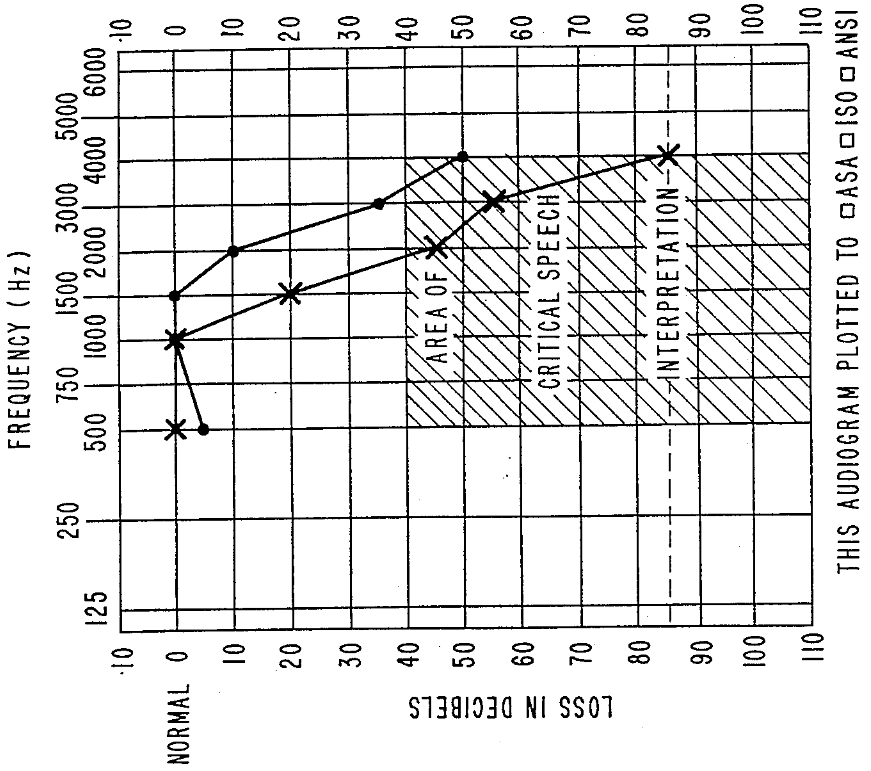
FIG. 8 is a graph of the hearing ability of the same patient, measured with a hearing aid, after dinner, with the harness being in place all through dinner.
Figure 7:
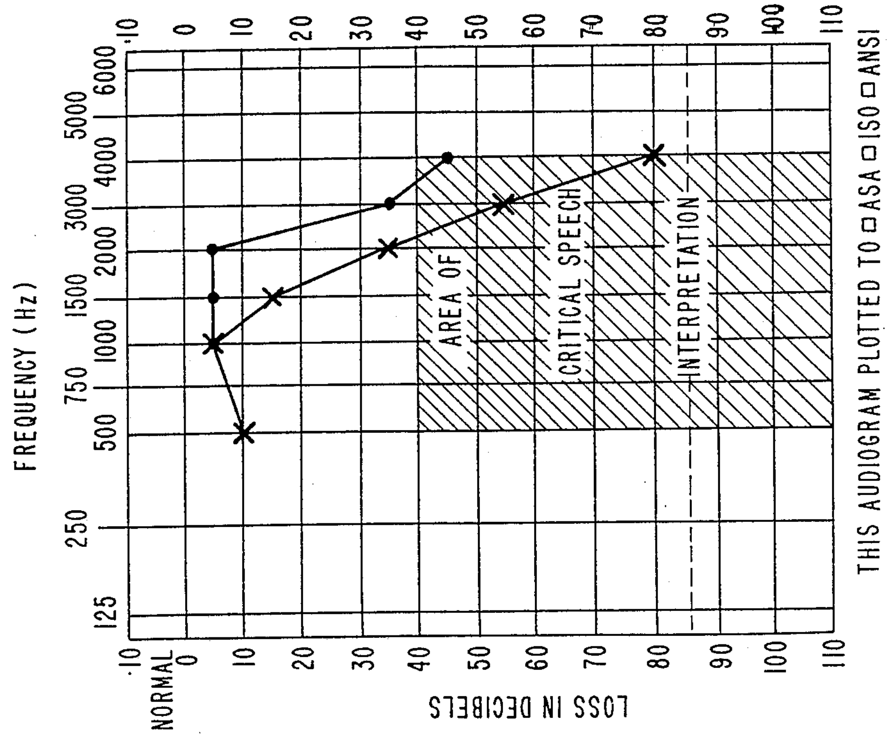
FIG. 7 is a graph of the hearing ability of the same patient, measured before dinner and with a hearing aid, and with the harness in place on the hearing aid.

FIGS. 5 and 6 show test results obtained without the use of a harness, and should be compared to the results shown in FIGS. 7 and 8 where a harness was used on the hearing aid.

FIG. 7 shows the same patient's hearing ability measured before dinner, wearing hearing aids with harnesses. The data shown in FIG. 7 are to be compared to the data shown in FIG. 8 which were measured after dinner.

The patient was fitted with the same hearing aids with the volume controls at the same setting as for the test results shown in FIG. 5. A hearing test was conducted before dinner and the results are shown in FIG.

7. FIG. 7 will serve as the baseline for evaluating the data shown in FIG. 8. The hearing aids were worn throughout a meal and conversation of the same duration as the previous meal. No feedback was experienced during the meal and hence no gain adjustments were required. The gain could be left at its original level resulting in no degradation of hearing ability. The results of the after dinner hearing test are shown in FIG. 8. As can be seen, FIG. 8 shows marked improvement over the results shown in FIG. 6, thus tending to support the claim that the harness reduces the tendency of the hearing aid to move in response to jaw muscle movement. Reduced movement in turn means that the gain of the hearing aid does not have to be decreased in order to avoid feedback. This allows the patient to keep the gain at a higher level and enjoy improved hearing.

Figure 9:
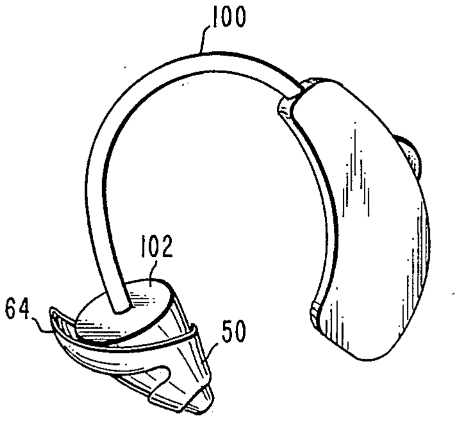
FIG. 9 shows use of the harness on the ear plug of a behind-the-ear type hearing aid.

The present invention can also be used with behind-the-ear hearing aids as shown in FIG. 9. In such hearing aids the microphone, amplifier and speaker are all located behind the ear. Sound is directed from the speaker down a tube 100 which is held in place in the ear by an ear-plug 102. The ear-plug may be fitted with the harness 50 to achieve many of the same benefits as achieved for the in-the-ear hearing aids as discussed herein.

Figure 10:
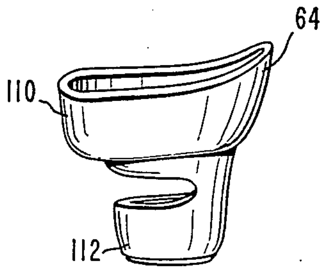
FIG. 10 shows a slight variation in the harness suitable for use on the mushroom-type hearing aids.

A slight alteration in the harness may be made to provide one large gasket 110 and a smaller gasket 112 as shown in FIG. 10 to accomodate the mushroom-type hearing aids.

Figure 11:
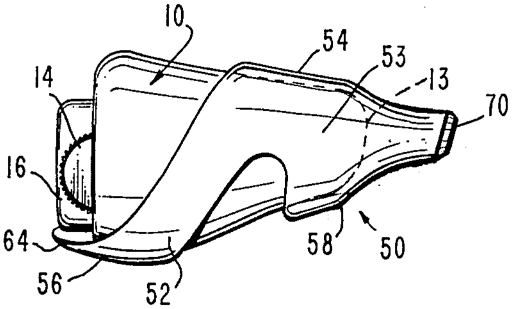
FIG. 11 shows a further variation in the shape of the harness, i.e., one of its ends extends away from the body of the hearing aid.

A further modification may be made to effect the embodiment shown in FIG. 11. As shown, the beveled end 70, which is of a smaller diameter than end 72, has been lengthened so as to extend beyond and away from the small end 13 of the hearing aid 10. The extension serves multiple purposes. First, the extension (or hood) creates a megaphone effect, channeling and directing the sound from the speaker located in the small end 13, toward the eardrum. Second, the hood serves as a sweeper or wiper during insertion of the hearing aid into the ear canal. The hood pushes aside ear wax so that it does not collect on the small end 13 of the hearing aid 10 and thereby block the small hole leading to the speaker. If the wax didn't collect on the "hood" it would clog the small hole and reduce the effectiveness of the speaker. Third, the hood extends away from the body of the hearing aid, thereby increasing the accoustic distance from the speaker to the microphone. Because sound from the speaker must travel a greater distance to reach the microphone, the intensity of the sound is reduced and the chance of the sound producing annoying feedback is thus also reduced.

For some applications the thickness of the wall of the harness will be uniform around the circumference of the harness. However, it is desirable to keep the harness wall as thin as practicable so that it can be used on existing hearing aids without unduly interfering with its close fit in the wearer's ear or causing discomfort. But if the wall is too thin, the walls of the notch 60 will not be thick enough to allow the skin to form a bulge 62 in the notch 60 and effect a locking relationship.

Figure 12:
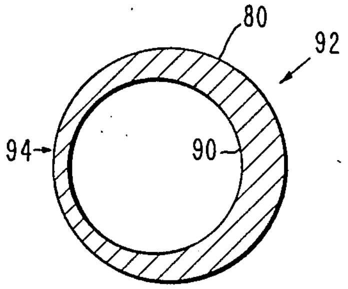
FIG. 12 illustrates an alternative cross sectional configuration for the harness, taken along the line 12—12 of FIG. 4.

The efffective or average thickness of the harness wall can be minimized, and the required wall thickness at the notch can be maintained, by forming the harness with the cross section shown in FIG. 12. The outer surface 80 of the harness is a generally circular surface (cylindrical surface), and the interior cylindrical surface 90 is formed eccentrically with respect to the outer surface. This allows the portion 92 to be thicker than portion 94. Notch 60 is formed in portion 92 and thus has thicker walls permitting the skin of the ear canal to form the required bulge 62 and complete its locking relationship with the notch 60. For purposes of illustration, the thin portion 94 may be 15 to 16 thousandths inch thick and the thick portion 92 may be about 20 thousandths inch.

Figure 13:
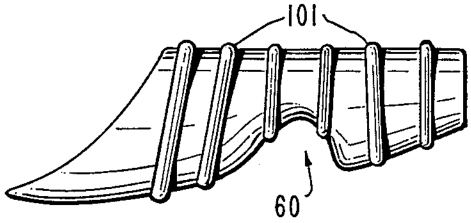
FIG. 13 shows the use of exterior circumferential ribs for additional protection against feedback.

Additional protection against acoustic feedback may be achieved by forming the harness with exterior ribs such as ribs 101 in FIG. 13. Circumferential grooves are made in the surface of the mandrel used to form the harness. The harness is formed on the mandrel and then removed from the mandrel and turned inside out. Any desired number of ribs 101 can be formed, depending on circumstances. The ribs, which may typically be 0.005 inch high, serve as baffles to further reduce the transmission of sound from the speaker, around the harness (between the harness and the ear canal wall), and into the microphone.

An additional benefit is produced by turning the harness inside out. In so doing, the inside smaller diameter surface 90 is stretched over the outside larger diameter surface 80. This tends to compress the material of the harness and cause it to flare radially outward wherever there is an opening, such as at the two ends and at the notch 60. The outward flaring tends to hold the harness tightly against the ear canal, further reducing the likelihood of acoustic feedback.

There has thus been described a simple, inexpensive harness which not only suppresses acoustic feedback but also resists the tendency of in-the-ear hearing aids to work themselves loose as a result of jaw muscle movement. At the same time, the unique shape of the harness provides a tab and a gasket thereby eliminating the possibility of a gasket falling off the narrow end of the hearing aid during removal and becoming lost in the ear canal. In addition, a significant advantage of the design of the harness is that it can be used with hearing aids of older design (i.e. the hearing aids that do not have electronic circuitry built in to suppress feedback) and can also be used with newer hearing aids which may be custom molded to the user's ear shape. The harness is easily retrofitted to a wide variety of types and sizes of hearing aids already in use.

While the harness of the present invention has been described with reference to the particular embodiments shown in the Figures, such Figures are for illustration purposes only and should not interpreted as placing specific limitations on the scope of the invention which is intended to be defined solely by the appended claims.

What is claimed is:

1. A harness for mounting on a portion of a hearing aid which fits in an ear canal of a user, said harness comprising:
   - a generally tubular member of resilient elastomeric material having a first end and a second end and a longitudinal centerline and having an opening in said first end which lies in a plane approximately perpendicular to the longitudinal centerline of the tubular member, and having an opening in said second end which lies in a plane which is at a substantial angle to the centerline; and
   - a notch in said tubular member located intermediate said first end and said second end, said notch extending substantially perpendicular to the longitudinal centerline.

2. A harness according to claim 1 wherein said first end is provided with an end opening of longitudinally tapered thickness.

3. A harness according to claim 1 wherein said angle lies between 30 and 60 degrees to the centerline.

4. A harness according to claim 3 wherein said angle is 45 degrees.

5. A harness according to claim 1 wherein the tubular member has walls having a thickness between 0.018 and 0.040 inches.

6. A harness according to claim 1 wherein said tubular member is made of silicon rubber.

7. A harness according to claim 1 wherein said notch is generally V shaped, having an open top end and an opposite bottom end.

8. A harness according to claim 7 wherein the bottom end of said V shaped notch is a smooth curved surface.

9. A harness according to claim 8 wherein said notch has a depth of from thirty to sixty percent of a diameter of said tubular member.

10. A harness according to claim 1 wherein said first end is lengthened such that when said harness is placed upon a hearing aid having a speaker mounted in one end thereof said first end extends beyond and away from the end of said hearing aid which houses said speaker.

11. A harness according to claim 1 wherein said tubular member has an interior cylindrical surface and an exterior cylindrical surface and the interior cylindrical surface of said tubular member is formed eccentrically with respect to the exterior cylindrical surface of said tubular member whereby said harness is provided with a wall having a thicker portion and a thinner portion.

12. A harness of claim 1 further including at least one circumferential rib located on the exterior cylindrical surface of said tubular member.

13. A harness for suppressing feedback associated with a hearing aid, said harness for mounting on a portion of the hearing aid which is placed in an ear canal a user comprising:

a first gasket;

a second gasket coupled to said first gasket along a portion of a perimeter of said second gasket and said first gasket; and a tab coupled to said first gasket of a length sufficient to extend outside the ear canal of said user;

whereby said tab is coupled to both said first gasket and second gasket such that the gaskets cannot fall off when the hearing aid is removed from the ear canal by pulling on said tab.

14. A harness of claim 13 wherein:

said first and second gaskets are generally tubular in shape and each of said gaskets has a longitudinal centerline and are coupled to one another such that the longitudinal centerline of each of said gaskets are generally coincident.

15. A harness of claim 14 wherein:

said tab is integrally formed with said first gasket.

16. A harness according to claim 13 wherein said second gasket has a longitudinal length sufficient such that when said harness is mounted on said hearing aid, said second gasket extends beyond and away from that end of the hearing aid which houses the speaker.

17. A harness according to claim 13 wherein said tubular member has an interior cylindrical surface and an exterior cylindrical surface and the interior cylindrical surface of said tubular member is formed eccentrically with respect to the exterior cylindrical surface of said tubular member whereby said harness is provided with a wall having a thicker portion and a thinner portion.

18. A harness of claim 13 further including at least one circumferential rib located on the exterior cylindrical surface of said tubular member.

19. A harness for mounting on a portion of a hearing aid which fits in an ear canal of a user, said harness comprising:

a generally tubular member of resilient elastomeric material having a first end and a second end, a longitudinal centerline and a diameter, said material being sufficiently elastomeric such that the tubular member can be expanded radially of said centerline to a diameter sufficient to receive said portion of said hearing aid; and a notch in said tubular member located intermediate said first end and said second end, said notch extending substantially perpendicular to the longitudinal centerline.

20. A harness of claim 19 wherein said first end is lengthened such that when said harness is placed upon a hearing aid having a speaker mounted in one end thereof, said first end extends beyond and away from the end of said hearing aid which houses said speaker.

21. A harness of claim 19 wherein said tubular member has an interior cylindrical surface and an exterior cylindrical surface defining a wall of said tubular member, and the interior cylindrical surface is formed eccentrically with respect to said exterior cylindrical surface whereby a thickness of said wall of said tubular member varies gradually from a location of least thickness to a location of greatest thickness.

22. A harness of claim 21 wherein said notch is formed in the location of greatest thickness of said wall.

* * * * *